(12) United States Patent
Olalde Rangel

(10) Patent No.: US 7,381,432 B2
(45) Date of Patent: Jun. 3, 2008

(54) MENOPAUSE DISORDER SYNERGISTIC PHYTO-NUTRACEUTICAL COMPOSITION

(75) Inventor: Jose Angel Olalde Rangel, Clearwater, FL (US)

(73) Assignee: Jose Angel Olalde, Clearwater, FL (US)

( * ) Notice: Subject to any disclaimer, the term of this patent is extended or adjusted under 35 U.S.C. 154(b) by 0 days.

(21) Appl. No.: 11/533,246

(22) Filed: Sep. 19, 2006

(65) Prior Publication Data

US 2008/0069909 A1  Mar. 20, 2008

(51) Int. Cl.
*A01N 65/00* (2006.01)
(52) U.S. Cl. .................................... 424/725
(58) Field of Classification Search .................... None
See application file for complete search history.

(56) References Cited

U.S. PATENT DOCUMENTS

| | | | |
|---|---|---|---|
| 5,162,037 A * | 11/1992 | Whitson-Fischman | 600/12 |
| 6,224,872 B1 * | 5/2001 | Shibuya et al. | 424/729 |
| 6,238,707 B1 * | 5/2001 | Chun | 424/725 |
| 2001/0046524 A1 * | 11/2001 | Ong et al. | 424/769 |
| 2003/0091659 A1 * | 5/2003 | Lu et al. | 424/727 |
| 2004/0071825 A1 * | 4/2004 | Lockwood | 426/72 |
| 2005/0048461 A1 * | 3/2005 | Lahteenmaki | 435/3 |
| 2005/0260287 A1 * | 11/2005 | DiMatteo-Leggio | 424/725 |
| 2005/0276873 A1 * | 12/2005 | Li | 424/773 |
| 2006/0073224 A1 * | 4/2006 | Last | 424/773 |

OTHER PUBLICATIONS

Syrov et al., Effect of Turkesterone and Nerobol on Activity of the Protein Synthesizing System in the Mouse Liver.Voprosy Meditsinskoi Khimii, (1978) vol. 24, No. 4, pp. 456-460.*
Dinan et al, Synthesis and biological activities of turkesterone 11[alpha]-acyl derivatives. Journal of Insect Science (Tucson), (2003) vol. 3, No. 6, pp. 1-11, 34 ref.*
Chernysh et al., Adaptation to Damage in the Silkworm Bombyx-Mori Lepidoptera Bombycidae 1. Effect of the Ecdysterone and Some Adaptogens on Larval Resistance to Formaldehyde Intoxication. Entomologicheskoe Obozrenie, (1981) vol. 60, No. 1, pp. 21-33.*

* cited by examiner

*Primary Examiner*—Michael Meller
*Assistant Examiner*—Qiuwen Mi

(57) ABSTRACT

A Phytoceutical composition for the prevention and treatment of menopause disorders and symptoms is provided. A specific combination of extracts of plants is taught, as well as principles for varying the formulations based on categorizing plants into one of three groups, Energy, Bio-Intelligence, and Organization and selecting several plants from each group. Such combinations have synergistic effects, with minimal side effects.

2 Claims, 1 Drawing Sheet

DRAWING # 1: CATEGORIZATION OF BENEFICIAL PLANTS AND NUTRACEUTICALS INTO THREE GROUPS, ENERGY, BIO-INTELLIGENCE AND ORGANIZATION.

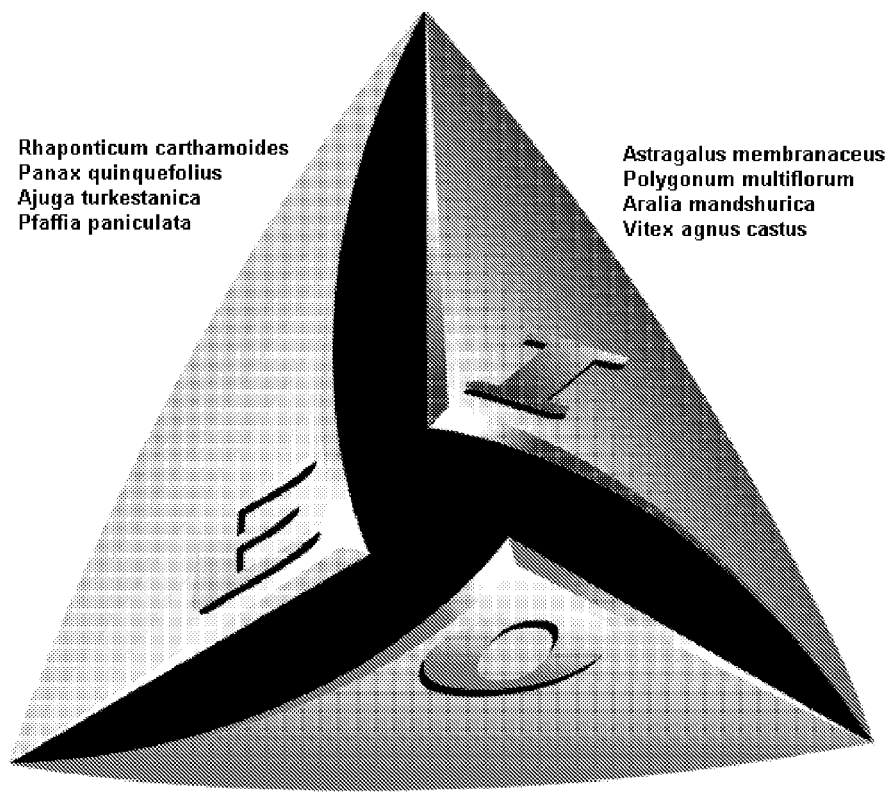

Rhaponticum carthamoides
Panax quinquefolius
Ajuga turkestanica
Pfaffia paniculata Astragalus membranaceus
Polygonum multiflorum
Aralia mandshurica
Vitex agnus castus Pueraria lobata, Cimicifuga racemosa, Dioscorea villosa, Angelica sinensis, Tribulus terrestres, Serenoa repens, Linum usitatissimum, Vitamin E

MENOPAUSE DISORDER SYNERGISTIC PHYTO-NUTRACEUTICAL COMPOSITION

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phytoceutical formulation used to treat menopause disorders and symptoms. The formulation is a particular combination of plants that have synergistic effect in combination. Principles for selecting beneficial formulations are provided.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process. As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines. A more recent study with additional demonstration concerning a phytomedicine's synergistic effect—Echinacea—is provided by Dalby-Brown et al, 2005. This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). *Conclusion*: On one hand, synthetics may have the required efficacy for disease treatment; however this can be marred by severe side effects. On the other hand, despite the excellent medicinal qualities of many plants, they are individually insufficient to take chronic degenerative diseases into remission. However, there is mounting evidence which demonstrates that medical plants contain synergistic efficacy and/or side-effect neutralizing combinations (Gilani and Rahman, 2005). Thus, what are needed in the art are better treatment regimes with improved patient tolerance, while providing sufficient efficacy.

SUMMARY OF THE INVENTION

A number of known beneficial plants were classified according to their capacity to enhance the three main elements that support overall health: Energy (E), Bio-intelligence (I) and Organization (O). A synergistic effect is expected when all three categories of herbs (E, I, O) are included in a formulation, preferably at least two or three or four plants from each category. Thus, one embodiment of the invention provides a method of selecting additional disease treating formulations according to these principles. An example of a formulation prepared this way is provided and additional formulations are being prepared and tested. As they reach menopause, a majority of women living in Westernized countries experience climacteric symptoms. The climacteric syndrome involves a variety of symptoms such as profuse sweating, insomnia, memory loss, decreased sexual drives, joint aches, and anxiety. However, amongst these symptoms, hot flashes and sweats are generally considered the hallmark and result in the majority of the medical consultations for this condition. Hormone replacement therapy (HRT) has been used to remediate these symptoms. Recent studies, however, have suggested that HRT may increase the risk of developing breast cancer and cardiovascular disease (CVD). Since ancient times, extracts of plants have been used for women's health to prevent menopausal symptoms. Therefore, many women are looking for alternative treatment options. Thus, another embodiment of the invention provides an effective, natural composition for treating menopause disorders and symptoms. The composition can be used alone, or can be combined with simultaneous use of one or more pharmaceutical compositions.

DETAILED DESCRIPTION OF THE INVENTION

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.2, 1.5, 2,5, or 10 fold.

By use of "plants," what is meant herein is that the plant (or that portion with medicinal activity) is used whole, ground, or as an extract. Also included are purified active ingredients and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only and should not serve to unduly limit the invention.

EXAMPLE 1

Plant Characteristics

Menopause Disorder and Symptoms

Energy Enhancing Phytoceuticals

Ajuga turkestanica: Its main active principle turkesterone, a phytoecdysteroid possessing an 11alpha-hydroxyl group. Ecdysteroids normalize NADH dehydrogenase activity, enzyme which catalyzes electron transfer from NADH to ubiquinones in the oxidative phosphorylation processes which occur at the mitochondrial level, contributing to the potential electrochemical buildup required to produce ATP. It also normalizes the succinate dehydrogenase enzyme which participates in the tricarboxilic acid cycle, which translates to ATP synthesis and patient energy level increases [Tashmukhamedova M A, Almatov K T, Syrov V N. Comparative study of the effect of ecdysterone, turkesterone and nerobol on the function of rat liver mitochondria in experimental diabetes. *Vopr Med. Khim.* 1986; 32:24-8].

*Panax quinquefolius* (American *Ginseng*, Anchi, Canadian *Ginseng*, Five Fingers, *Ginseng*, American, North American *Ginseng*, Red Berry, Ren Shen, and Tienchi) is related to *Panax ginseng*, but is a distinct species with higher levels of ginsenoside Rb1 and without ginsenoside Rf. These substances confer energizing properties because they increase ATP synthesis. It also has antioxidant and anti-inflammatory effects. Results of clinical research studies demonstrate that *Panax quinquefolius* improves physical and mental performance and increases resistance to exogenous stress factors. The incorporation of this phytomedicine provides at least 206 active principles in a single therapeutic.

*Pfaffia paniculata* (Suma, Brazilian Ginseng, *Pfaffia*, Para Tudo, Corango-acu; also *Hebanthe paniculata, Gomphrena paniculata, G. eriantha, Iresine erianthos, I. paniculata, I. tenuis, P. eriantha, Xeraea paniculata*) contains active glycosides (beta-ecdysone and three ecdysteroids), six different pfaffic acids, phytosterols (sitosterol and estigmasterol). *Pfaffia* also contains saponins and 19 different amino acids, minerals, vitamins and pantoneic acid. Its germanium content probably accounts for its properties as an oxygenator at the cellular level, and its high iron content may account for its traditional use for anemia. This herb increases energy through an increase in ATP synthesis and oxygenation at the cellular level, and it also has anabolic activity at the muscular level. These substances act as hormone precursors modulating estrogen, progesterone and testosterone production (Oshima M, Gu Y. *Pfaffia paniculata*-induced changes in plasma estradiol-17beta, progesterone and testosterone levels in mice. J Reprod Dev. 2003; 49: 175-80) and have demonstrated effectivity in the management of diverse conditions related to hormone unbalance such as menopause (Pitchford, Paul. Healing With Whole Foods: Asian Traditions and Modern Nutrition. North Atlantic Books; 3rd Edition; 2002. ISBN: 1556434308). Suma has safe estrogenic activity because of its store of sitosterol, a compound which increases body's natural estrogen. Incorporation of *Pfaffia* provides 44 active principles.

*Rhaponticum carthamoides* (Leuzea, or Maral Root) contains a mixture of compounds called 'levseins'. Levseins represents a complex of more than 10 ecdysterones including 20-beta-ecdysterone, makisterone C, 24-dehydromakisterone A, carthamosterone, polypodyne B and ajugasterone C. Ecdysteroids normalize NADH dehydrogenase activity, enzyme which catalyzes NADH electron transfer to the ubiquinone in the oxidative phosphorylation processes at the mitochondrial level, contributing to buildup the electrochemical potential used to produce ATP. It also normalizes the succinate dehydrogenase activity, enzyme which acts in the tricarboxilic acid cycle, which translates in ATP synthesis and patient energy level increases. In women with low levels of estrogens, Ecdysterone behaves as an anabolic steroid mimicking the effects of these hormones. Incorporation of this phytomedicine in a composition provides at least 10 active principles in a single therapeutic.

Bio-Intelligence Modulators

*Aralia mandshurica* (Manchurian Thorn Tree) The main active principles are triterpene saponins aralosides (elatosides). Siberians traditionally preferred *Aralia* for immune health, to reduce stress/depression, and to improve physical and mental performance. Siberians would often combine *Aralia* with other adaptogens for maximal stress reduction/performance enhancement benefits. *Aralia* extract was included in the official Russian Pharmacopoeia in 1983 as a treatment for the symptoms of stress overload, such as fatigue, weakness, headache, libido loss, depression, immune weakness, etc. G. P. Gubina reported in 1988 a 90 percent success rate—using *Aralia*—in 106 patients treated for various "asthenic" (stress overload/weakness) conditions. *Aralia* enhances a person's ability for memorization and prolonged concentration. In proofreading tests, after taking this plant, a decrease in the quantity of mistakes was observed in 88 percent of the experimental group, while an increase in the quantity of mistakes was observed in 54 percent of the control group. Those taking *Aralia mandshurica* exerted a strong stimulating influence among test subjects who displayed a great improvement in reading comprehension, aptitude and speed. [A. A. Lebedev/Far East Scientific Center of the USSR]; [V. V. Kazakevich/Academy of Sciences, Vladivostok, Russia].

*Astragalus membranaceus* (Huang-Qi, Huangqi) This plant contains three main types of active principles. Isoflavones, principalmente Formononetin, astragalans, and astragalosides which act as modulators of the hypothalamus-hypofisis-adrenal axis response. It also contains linoleic acid. Formononetin has Estrogenic Receptor alpha and beta binding affinity (Halabalaki M, Alexi X, Aligiannis N. Estrogenic activity of isoflavonoids from *Onobrychis ebenoides*. Planta Med. 2006; 72: 488-93). Dietary supplements are currently used to treat menopausal symptoms because of their high content of the mildly estrogenic isoflavones (formononetin). This compound is estrogenic in vitro and in vivo (Booth N L, Overk C R, Yao P. Seasonal variation of red clover (*Trifolium pratense* L., Fabaceae) isoflavones and estrogenic activity. J Agric Food Chem. 2006; 54: 1277-82).

Isoflavones have a high affinity to estrogen receptor alpha (ERalpha), estrogen receptor beta (ERbeta), progesterone receptor (PR) and androgen receptor (AR). The affinity to ER has been used as an explanation of the effects of isoflavones in the treatment of menopausal disorders. Biochemical analysis shows that phytoestrogens have multiple actions beside selective estrogen receptor modulator (SERM)-activity. They act as selective estrogen enzyme modulators (SEEMs), have antioxidant activity and interact with transcription factors such as NF-kappaB. Furthermore, it is indicated that they have protective effects on osteoporosis and the cardiovascular system (Beck V, Rohr U, Jungbauer A. Phytoestrogens derived from red clover: an alternative to estrogen replacement therapy? J Steroid Biochem Mol. Biol. 2005; 94: 499-518). Formononetin showed clear estrogenic activity through estrogen receptor alpha (ERalpha) and estrogen receptor beta (ERbeta) and affinity to progesterone (PR) and androgen (AR) receptors. In vitro assays and chemical analysis showed that theoretical estrogenic activity expressed as equivalent E2 concentration is in the same range as recommended for synthetic estrogens. Broader spectrum of action and hypothesized lower side effects by action through ERbeta make them suitable for alternative hormone replacement therapy (Beck V, Unterrieder E, Krenn L. Comparison of hormonal activity (estrogen, androgen and progestin) of standardized plant extracts for large scale use in hormone replacement therapy. J Steroid Biochem Mol. Biol. 2003; 84: 259-68). Formononetin binds well to human ER beta and human ER alpha (Morito K, Aomori T, Hirose T. Interaction of phytoestrogens with estrogen receptors alpha and beta (II). Biol Pharm Bull. 2002; 25: 48-52). *Astragalus* offers 38 active principles in a single therapeutic.

*Polygonum multiflorum* (Fo-Ti, Chinese Knotweed, Chinese Cornbind, Climbing Knotweed, Flowery Knotweed, Fleeceflower, He Shou Wu) The main constituents of *Polygonum multiflorum* are: emodin, chrysophanol, rhein, 6-OH-emodin, emodin-8-beta-D-glucoside, polygonimitin B, 2,3,5,4'-tetrahydroxystilbene-2-O-beta-D-glucoside, gallic acid. This pkant has been used traditionally in China for menopause symptoms management. *Polygonum* has estrogenic activity (Kang S C, Lee C M, Choi H. Evaluation of oriental medicinal herbs for estrogenic and antiproliferative activities. Phytother Res. 2006 Aug. 14). Another study which gives support to the reported efficacy of Chinese medicines used for hormone replacement therapy is Zhang C Z, Wang S X, Zhang Y. In vitro estrogenic activities of Chinese medicinal plants traditionally used for the management of menopausal symptoms. J. Ethnopharmacol. 2005; 98: 295-300). *Polygonum* provides 47 active principles in a single therapeutic.

*Vitex agnus castus* (Chasteberry, Chaste-Tree): From the fruit of this plant are obtained an essential oil, linoleic acid, two iridoid glicosides (aucubine y el agnusine); a flavone (casticin), flavonoids derived from kaempferol and quercetagine and other flavonoids such as penduletin, vitexin and apigenin. Penduletin and apigenin, flavonoids of *Vitex agnus castus* are estrogenic compounds. Both substances are specific ligands for the beta-estrogenic receptor (Jarry H, Spengler B, Wuttke W. In vitro assays for bioactivity-guided isolation of endocrine active compounds in *Vitex agnus-castus*. Maturitas. Epub Aug. 21, 2006). Extracts of *Vitex agnus-castus* displace estradiol from Estrogenic Receptor alpha and beta. Linoleic acid is one possible estrogenic component of the extract. Linoleic acid is an Estrogenic Receptor ligand. These data suggest that linoleic acid from the fruits of *Vitex agnus-castus* can bind to estrogen receptors and induce certain estrogen inducible genes (Liu J, Burdette J E, Sun Y. Isolation of linoleic acid as an estrogenic compound from the fruits of *Vitex agnus-castus* L (chaste-berry). Phytomedicine. 2004; 11: 18-23). A clinical trial on 23 menopausal patients with essential oils of *Vitex agnus castus* indicated strong symptomatic relief of common menopausal symptoms. A second clinical trial on 52 additional subjects appears to support the finding of the first trial (Chopin Lucks B. *Vitex agnus castus* essential oil and menopausal balance: a research update Complement Ther Nurs Midwifery. 2003; 9: 157-60). Essential oils from *Vitex agnus castus* were found to be effective, in menopausal balance (Lucks B C, Sorensen J, Veal L. *Vitexagnus-castus* essential oil and menopausal balance: a self-care survey. Complement Ther Nurs Midwifery. 2002; 8: 148-54). *Vitex agnus* preparations are commonly used for the treatment of menopausal symptoms.

Organizational Improvers

*Angelica sinensis* (Dong quai or *Angelica*, also *Angelica archangelia, Angelica pubescens* and *Angelica sylvestris* Can qui, Angelica china, dangdanggui, dang gui, dong quai, duong qui, handanggui, hashyshat almalak, kara toki, langdu danggui, min-gui, tang-kuei, tangkuei, tân q ui) Contains terpenes (terpenes, mainly β-phellandrene, with β-bisabolene, β-caryophyllene, β-phellandrene, α- and β-pinene, limonene, linalool, borneol, acetaldehyde, menthadienes and nitromenthadienes), macrocyclic lactones (including tridecanolide, 12-methyl tridecanolide, pentadecanolide), phthalates (such as hexamethylphthalate), coumarins (especially furocoumarin glycosides such as marmesin and apterin), angelicin and byakangelicin derivatives (osthol, umbelliferone, psoralen, bergapten, imperatoren, xanthotoxol, xanthotoxin, oxypeucedanin and more), as well as various sugars, plant acids, flavonoids, and sterols. It also, contains alkyl phthalides (Ligustilide); terpenes, phenylpropanoids (ferulic acid) and benzenoids. The results of a study demonstrated the estrogenic nature of the extract of *Angelica* (Circosta C, Pasquale R D, Palumbo D R. Estrogenic activity of standardized extract of *Angelica sinensis*. Phytother Res. 2006; 20: 665-9). A placebo-controlled trial on 55 postmenopausal women who complained of hot flushes and refused hormonal therapy showed a significant difference between the study group and the control group in the decrease in number and intensity of hot flushes from baseline to completion of treatment. There was also a marked alleviation of sleep disturbances and fatigue (Kupfersztain C, Rotem C, Fagot R. The immediate effect of natural plant extract, *Angelica sinensis* and *Matricaria chamomilla* (Climex) for the treatment of hot flushes during menopause. A preliminary report. Clin Exp Obstet Gynecol. 2003; 30: 203-6). Dong quai showed weak Estrogen Receptor binding and Progesteron Receptor and pS2 mRNA induction. These data suggest a potential use in the treatment of menopausal symptoms (Liu J, Burdette J E, Xu H. Evaluation of estrogenic activity of plant extracts for the potential treatment of menopausal symptoms. J Agric Food Chem. 2001; 49: 2472-9). Angelica provides 70 active principles.

*Cimicifuga racemosa* (Black Cohosh, Black Snakeroot): Key active constituents are: triterpene glycosides (containing a cyclopropane ring) including acetein, cimicifugoside and racemoside; isoflavones including formononetin; aromatic acids including isoferulic acid and salicylic acid. Also tannin, resin (cimicifugin), ranunculin, fatty acids, starch and sugars. A multicenter, randomized, placebo-controlled, double-blind, parallel group study was conducted in 122 menopausal women. The results indicate a superiority of *Cimicifuga racemosa* extract compared to placebo in patients with menopausal disorders (Frei-Kleiner S, Schaffner W, Rahlfs V W. *Cimicifuga racemosa* dried ethanolic extract in menopausal disorders: a double-blind placebo-controlled clinical trial. Maturitas. 2005; 51: 397-404). A clinical trial studied the changes in subjective symptoms of menopause in 2016 women treated with an extract of *Cimicifuga racemosa*. The most favorable changes were found in hot flashes, sweating, insomnia, and anxiety. The extract of *C. racemosa* was found to be effective in the alleviation of menopausal symptoms (Vermes G, Banhidy F, Acs N. The effects of remifemin on subjective symptoms of menopause. Adv Ther. 2005; 22: 148-54). In a randomized clinical controlled study on climacteric complaints, the extract of *Cimicifuga racemosa* significantly reduced the number of hot flushes per day and vasomotor symptoms. CONCLUSIONS: CR may be a valid alternative in the management of climacteric complaints in those women who cannot be treated with or just refuse conventional strategies (Nappi R E, Malavasi B, Brundu B. Efficacy of *Cimicifuga racemosa* on climacteric complaints: a randomized study versus low-dose transdermal estradiol. Gynecol Endocrinol. 2005; 20: 30-5). Black cohosh has been used in the US for over 100 years. Review of the published clinical data suggests that *cimicifuga* may be useful for the treatment of menopausal symptoms, such as hot flashes, profuse sweating, insomnia, and anxiety (Mahady G B. Black cohosh (*Actaea/Cimicifuga racemosa*): review of the clinical data for safety and efficacy in menopausal symptoms. Treat Endocrinol. 2005; 4: 177-84). Osmers R, Friede M, Liske E. Efficacy and safety of isopropanolic black cohosh extract for climacteric symptoms. Obstet. Gynecol. 2005; 105: 1074-83. This randomized, multicenter, double-blind clinical trial compared the efficacy and tolerability of the black cohosh extract in the treatment of climacteric complaints compared with placebo in a total of 304 patients. The results showed that the black cohosh extract was more effective than placebo and clinically relevant. *Cimicifuga* contains at least 45 active principles in a single therapeutic.

*Dioscorea villosa* (Mexican wild yam, china root, colic root, rheumatism root, huesos del diablo, yuma.) contains steroid sapogenins (dioscine, dioscorin and diosgenine) as the main active principles. It also contains salts and minerals, such as: aluminum, calcium, chrome, cobalt, iron, selenium, silica, sodium, tin, zinc, magnesium, manganese, phosphorus and potassium; and vitamins: ascorbic acid, beta-carotene, niacin, riboflavin and thiamine. Diosgenine can be transformed into pregnenolone, and progesterone [Gareth, Thomas. Medicinal Chemistry. John Wiley & Sons; First edition December 2000. ISBN: 0471489352]. The starting material for the production of progesterone is diosgenin obtained from a number of *Dioscorea* species (a plant source). Diosgenin may be converted to pregnenolone acetate by a series of steps. Wild yam is used as a precursor in the manufacture of "natural progesterones". Natural progesterone products help reduce hot flashes or improve vaginal health [Tagliaferri, Mary. The New Menopause Book. Avery Publisher; March, 2006]. A clinical controlled trial in 24 postmenopausal women showed that *Dioscorea* significantly increases serum concentrations of estrone, sex hormone binding globulin, and estradiol. Although the exact mechanism is not clear, *Dioscorea* improves the status of sex hormones (Wu W H, Liu L Y, Chung C J. Estrogenic effect of yam ingestion in healthy postmenopausal women. J Am Coll Nutr. 2005; 24: 235-43). The incorporation of this phytomedicine provides at least 29 active principles in a single therapeutic.

*Linum usitatissimum* (Flaxseed, Flax, Linseed) Phytoestrogens are diphenolic compounds that are present in several plants eaten by human beings. Flaxseed is particularly abundant source of phytoestrogens. Phytoestrogens have been shown to have significant estrogen agonists/antagonists effects in animals and humans. There is epidemiological, laboratory and clinical evidence which indicates that phytoestrogens, like certain selective estrogen receptor modulators, have a positive effect on the lipoprotein profile and bone density. They might also improve some of the climacteric symptoms. (Brzezinski A, Debi A. Phytoestrogens: the "natural" selective estrogen receptor modulators? Eur J Obstet Gynecol Reprod Biol. 1999; 85: 47-51). Phytoestrogens, which are abundant in flaxseed, have chemical structures resembling those of endogenous estrogens and have been shown to exert hormonal effects. A clinical, randomized, controlled trial in 46 postmenopausal women supplemented with either a placebo, soy, or flaxseed for 16 wk showed that urinary concentrations of 2-hydroxyestrone increased significantly in the flaxseed group. In the soy and placebo groups, no significant correlation was observed. CONCLUSIONS: Supplementation with flaxseed modifies urinary estrogen metabolite excretion to a greater extent than does supplementation with an equal amount of soy (Brooks J D, Ward W E, Lewis J E. Supplementation with flaxseed alters estrogen metabolism in postmenopausal women to a greater extent than does supplementation with an equal amount of soy. Am J Clin Nutr. 2004; 79: 318-25). A clinical, randomized, controlled trial showed that Flaxseed is as effective as oral estrogen-progesterone to improve mild menopausal symptoms. (Lemay A, Dodin S, Kadri N. Flaxseed dietary supplement versus hormone replacement therapy in hypercholesterolemic menopausal women. Obstet. Gynecol. 2002; 100: 495-504). A clinical, randomized, controlled trial examined the effects of flaxseed consumption on urinary estrogen metabolite excretion in 28 postmenopausal women showed that Flaxseed supplementation significantly increased urinary 2-OHEstrogen excretion and the urinary $2/16$ alpha-OHE1 ratio. Results suggest protective effects in postmenopausal women (Haggans C J, Hutchins A M, Olson B A. Effect of flaxseed consumption on urinary estrogen metabolites in postmenopausal women. Nutr Cancer. 1999; 33: 188-95). *Linum usitatissimum* contains Linoleic acid, an Estrogenic Receptor ligand that can bind to estrogen receptors and induce certain estrogen inducible genes (Liu J, Burdette J E, Sun Y. Isolation of linoleic acid as an estrogenic compound from the fruits of *Vitex agnus-castus* L. (chaste-berry). Phytomedicine. 2004; 11: 18-23). The seeds of *Linum* contain 117 active principles.

*Pueraria lobata* (Kudzu): the active components in kudzu root are the isoflavones puerarin, daidzin, genistin, daidzein, and genistein. *Pueraria lobata* has high estrogenic relative potency (Kang S C, Lee C M, Choi H. Evaluation of oriental medicinal herbs for estrogenic and antiproliferative activities. Phytother Res. Advance Epub 2006, Aug. 14). A clinical trial of a nutritional supplement containing isoflavones from kudzu and red clover, along with other targeted nutrients on menopausal symptoms and markers of breast cancer and CVD risk, carried out in twenty-five menopausal women suffering from severe hot flushes and night sweats showed a 46% decrease in reported hot flushes. Quality of life showed similar improvement. The results of this trial suggests that this combination isoflavone nutritional supplement may significantly relieve the most troubling symptoms of menopause, as well as confer some chemopreventive and cardioprotective benefits (Lukaczer D, Darland G, Tripp M. Clinical effects of a proprietary combination isoflavone nutritional supplement in menopausal women: a pilot trial. Altern Ther Health Med. 2005; 11:60-5). Estrogenic activity of the Chinese herb kudzu root was investigated by a recombinant yeast screening assay (YES). The crude extract and its sub-fractions, showed clear estrogenic activity. The results showed that the high content of isoflavones as well as the high estrogenic activity could make kudzu root extract an interesting candidate for hormone replacement therapy (Zhang Y, Chen J, Zhang C. Analysis of the estrogenic components in kudzu root by bioassay and high performance liquid chromatography. J Steroid Biochem Mol. Biol. 2005; 94: 375-81). *Pueraria lobata* showed estrogenic activity which explains its reported efficacy for the treatment of menopausal symptoms (Zhang C Z, Wang S X, Zhang Y. In vitro estrogenic activities of Chinese medicinal plants traditionally used for the management of menopausal symptoms. J. Ethnopharmacol. 2005; 98: 295-300). Pueraria radix has effective estrogenic actions and could be developed as estrogenic supplement (Kim O S, Choi J H, Soung Y H. Establishment of in vitro test system for the evaluation of the estrogenic activities of natural products. Arch Pharm Res. 2004; 27: 906-11). Results of another showed that puerarin and total pueraria isoflavones acted as weak estrogen-like effect on estrogen-deficiency animals, while no effect on normal-estrogen level ones, but as antiestrogen-like effect in high-estrogen-level ones. Results suggested that puerarin and TIP possessed property of partial agonist of estrogen receptor (Zheng G, Zhang X, Zheng J. Estrogen-like effects of puerarin and total isoflavones from *Pueraria lobata*. Zhong Yao Cai. 2002; 25: 566-8). *Puirura* contains at least 26 active principles.

*Serenoa repens* (Saw palmetto, *Sabal serrulata*, Scrub-Palmetto). Its main active principles are saturated fatty acids: lauric, myristic, palmitic, capric, caprylic; and unsaturated fatty acids: oleic, linoleic and linolenic. These fatty acids have demonstrated inhibiting action on 5-Alpha-Reductase, enzyme which transforms Testosterone into Dihydrotestosterone (Raynaud J P, Cousse H, Martin P M. Inhibition of type 1 and type 2 5alpha-reductase activity by free fatty acids, active ingredients of Permixon. J Steroid Biochem Mol. Biol. 2002; 82: 233-9). Estrogens are manufactured from androstenedione or testosterone as immediate precursors. When the Testosterone into Dihydrotestosterone transformation is inhibited, Testosterone levels are improved; which is used in the biosynthesis of estrone, estradiol and estriol, deficient hormones during menopause. *Serenoa repens* contains Linoleic acid, an Estrogenic Receptor ligand that can bind to estrogen receptors and induce certain estrogen inducible genes (Liu J, Burdette J E, Sun Y. Isolation of linoleic acid as an estrogenic compound from the fruits of *Vitex agnus-castus* L. (chaste-berry). Phytomedicine. 2004; 11: 18-23). *Serenoa* contains 13 active principles.

*Tribulus terrestris* (Puncture Vine, Caltrop, Yellow Vine, bindy eye, bindii, bullhead, burnut, burra gokhroo, caltrop, calthrops, cat's head, common dubbeltjie, devil's thorn, devil's weed, doublegee, dubbeltje, goathead, gokshura, Maltese cross, Mexican sandbur, puncture vine, puncture weed, rose, small caltrops, tackweed, Texas sandbur, yellow vine and Goathead). The fruits and roots of *Tribulus* contain active principles such as: phytosterols, flavonoids, alkaloids, glucosides and steroidal saponins of the furostanol sub-class with a predominant amount of protodioscine (no less than 45%) which seems to be the principle that produces the clinical results. These active principles exert an effective stimulant effect over the reproductive systems, with the increase in body mass, vigour and resistance. Protodioscin is a phytochemical agent derived from Tribulus terrestris plant that is converted by the supra renal glands into DHEA [De-Hydro-Epi-Androsterone] (Adimoelja A. Phytochemicals and the breakthrough of traditional herbs in the management of sexual dysfunctions. Int J. Androl. 2000; 23: 82-4) constituting the raw material for the production of testosterona and estrogens, as well as other hormones. DHEA production declines with age. When the organism reaches 60 years it produces only between 5 and 15% of the normal amount, thus contributing to the ageing process. DHEA is transformed into Androstenedione and Testosterone, and later into Estrone and Estradiol, hormones which are lacking during menopause. Results of various studies sugest that DHEA supplements improve the symptoms of menopause, libido and osteoporosis in women. Significantly increasing levels of estradiol, luteinizing (LH) and foliculestimulating hormone (FSH). This way Tribulus improves the reproductive functions in women. Tribulus contains 46 active principles in a single therapeutic.

Vitamin E: From the Practice Guideline of the North American Menopause Society "In women who need relief for mild vasomotor symptoms, the North American Menopause Society recommends first considering lifestyle changes, either alone or combined with a nonprescription remedy, such as dietary isoflavones, black cohosh, or vitamin E" (italics by inventor) (Treatment of menopause-associated vasomotor symptoms: position statement of The North American Menopause Society. Menopause. 2004; 11: 11-33). For mild symptoms that do not interfere with sleep or daily function, behavioral changes in conjunction with vitamin E (800 IU/d) use is a reasonable initial approach for the management of menopause (Shanafelt T D, Barton D L, Adjei A A. Pathophysiology and treatment of hot flash).

EXAMPLE 2

Composition

Menopause Disorders

A particularly preferred composition is shown in Table 1. Ratios reflect the concentration of active ingredient over the natural state, and the amounts provided are mg of extract. Obviously, the amount should be increased where the strength is reduced, and vice versa.

TABLE 1

Phyto-Nutraceutical Composition

| Active Agent | Ratio | Amount (mg) |
|---|---|---|
| Energy enhancers | | |
| Ajuga turkestanica | 4:1 | 27 |
| Panax quinquefolius | 4:1 | 82 |
| Pfaffia paniculata | 4:1 | 82 |
| Rhaponticum carthamoides | 6:1 | 11 |
| Bio-Intelligence modulators | | |
| Aralia mandshurica | 4:1 | 27 |
| Astragalus membranaceus | 4:1 | 27 |
| Poligonum multiflorum | 4:1 | 27 |
| Vitex agnus castus | 4:1 | 82 |
| Organization improvers | | |
| Angelica sinensis | 4:1 | 82 |
| Cimicifuga racemosa | 4:1 | 82 |
| Dioscorea villosa | 4:1 | 82 |
| Linum usitatissimum | 4:1 | 82 |
| Pueraria lobata | 4:1 | 82 |
| Serenoa repens | 4:1 | 27 |
| Tribulus terrestris | 4:1 | 82 |
| Vitamin E | 1:1 | 16 |
| Total | | 900 |

EXAMPLE 3

Tolerance and Effectivety Study with Phytonutraceutical Composition

The effects of a phytonutraceutical composition—formulated under the precepts of Systemic Medicine—were examined for tolerance and effectiveness in 104 patients diagnosed with menopause through a retrospective, multicenter, descriptive 2 year study.

The composition improved in a high percentage of patients the following somatic alterations: vasomotor symptoms (92.8%), sleep disorders (88.2%) %), tachycardia (88.9%), arthralgias and myalgias (80.7%). An important percentage referred an improvement in the psicological alterations associated with menopause such as: Irritability (88.3%), Depression (88.9%), Physical and Mental tiredness (92.2%). 55% of the patients referred an abscense of urogenital disorders after the treatment. Quality of Life improved in the majority of patients. Tolerability was excellent; only one patient was affected (dyspepsia) representing less than one percent of the population (0.96%). The formulation created under the principles of Systemic Medicine demonstrated to be an effective treatment of the physical and psychological climacteric symptoms; reason for which it should be considered an effective therapeutic alternative.

EXAMPLE 4

Principles for Selecting Synergistic Combinations

In order to explain the range of formulations encompassed by the invention, we have categorized beneficial plants and nutraceutical into one of three groups, each of which should be present for synergistic effect. The classifications are: Energy, Bio-Intelligence and Organization. Plants and nutraceuticals classified under Energy are associated with ATP synthesis (such as the Krebs cycle, oxidative phosphorylation, beta-oxidation, etc.). Plants and nutraceuticals classified under Bio-Intelligence are those that regulate the neuroendocrine and immunological systems and cellular processes, thus controlling the interactions between the various systems in the body. Finally, plants and nutraceuticals classified under Organization are those that relate to the structure and function of specific organs. Combinations of plants and nutraceuticals from these three classification groups have synergistic effect because they address each necessary component of cellular and organic health—in effect they provide the triangle on which healing is fully supported. This triangle is depicted in Drawing #1.

An illustrative example of synergy in medicinal plants is an in vitro study that demonstrates how the activity of herbal Berberine alkaloids is strongly potentiated by the action of 5'-methoxyhydnocarpin (5'-MHC)—an active principle of another phytomedicine (denominated Hydnocarpus wightiana). It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. 2000; 97: 1433-7.

A further demonstration may be provided of synergistic effect on a molecular scale by studying the gene expression profile changes in response to various plant/nutraceutical ingredients and combinations thereof. Experiments are already underway demonstrating the expression profile in response to the formulations.

We will be aided in this work because researchers have already begun studying the expression profiles of various medicinal plants, thus providing a database of knowledge from which to build. E.g., Gohil, et al., mRNA Expression Profile of a Human Cancer Cell Line in Response to *Ginkgo Biloba* Extract: Induction of Antioxidant Response and the Golgi System, Free Radic Res. 2001; 33: 831-849.

Finally there may be further presentation of gene expression results using whole-genome microarray analysis to demonstrate the formulation's capability to provide gene activation (upregulation or downregulation).

What is claimed is:

1. A phytoceutical composition comprising: 27 mg of *Ajuga turkestanica,* 82 mg of *Panax quinquefolius,* 82 mg of *Pfaffia paniculata,* 11 mg of *Rhapontium carthamoides,* 27 mg of *Aralia mandshurica,* 27 mg of *Astragalus membranaceus,* 27 mg of *Polygonum multiflorum,* 82 mg of *Vitex agnus castus,* 82 mg of *Angelica sinensis,* 82 mg of *Cimicifuga racemosa,* 82 mg of *Dioscorea villosa,* 82 mg of *Linum usitatissimum,* 82 mg of *Pueraria lobata,* 27 mg of *Serenoa repens,* 82 mg of *Tribulus terrestris* and 16 mg of Vitamin E together with pharmaceutically acceptable excipients.

2. A method of treating menopause comprising administering an effective amount of the composition of claim 1 to a menopausal patient which is sufficient to alleviate said menopause.

* * * * *